United States Patent
Huang

(10) Patent No.: US 7,129,398 B2
(45) Date of Patent: Oct. 31, 2006

(54) REVERSIBLE MALE STERILITY IN TRANSGENIC PLANTS BY EXPRESSION OF A GA-INSENSITIVE MUTANT PROTEIN, GAI.

(75) Inventor: Shihshieh Huang, Stonington, CT (US)

(73) Assignee: Monsanto Technology LLC, St. Louis, MO (US)

(*) Notice: Subject to any disclaimer, the term of this patent is extended or adjusted under 35 U.S.C. 154(b) by 398 days.

(21) Appl. No.: 10/065,800

(22) Filed: Nov. 20, 2002

(65) Prior Publication Data

US 2003/0097672 A1    May 22, 2003

Related U.S. Application Data

(60) Provisional application No. 60/331,953, filed on Nov. 21, 2001.

(51) Int. Cl.
*C12N 15/82* (2006.01)
*C12N 15/29* (2006.01)
*A01H 1/00* (2006.01)
*A01H 1/02* (2006.01)
*A01H 5/00* (2006.01)
*A01H 5/10* (2006.01)

(52) U.S. Cl. .................. 800/303; 800/274; 800/278; 800/287; 800/290; 800/320.1; 504/103

(58) Field of Classification Search ............. 800/274, 800/278, 287, 290, 303, 320.1; 504/103
See application file for complete search history.

(56) References Cited

U.S. PATENT DOCUMENTS 6,258,999 B1 * 7/2001 Tomes et al. ............. 800/300.1

6,603,064 B1 * 8/2003 Van Dun et al. ........... 800/303

FOREIGN PATENT DOCUMENTS

WO    WO 97/29123 A2    8/1997

OTHER PUBLICATIONS

Peng et al. Nature 400: 256-261 (Jul. 1999).*
Koornneet at al. Theoretical and Applied Genetics 58(6): 257-263 (Nov. 1980)—Abstract only.*
Singh et al. Plant Science 86(2): 147-154 (1992).*
Singh et al. Journal of Experimental Botany 43: 1497-1505 (Nov. 1992).*
Shukla et al. Journal of Experimental Botany 44: 1497-1505 (Sep. 1993).*
Huang et al. Plant Physiology 131(3): 1270-1282 (Mar. 2003).*
Ahokas et al. Proceedings of the National Academy of Sciences USA 79(24): 7605-7608 (Dec. 1982).*
M. Ogawa et al, "Rice gibberellin-insensitive gene homolog, OsGAI, encodes a nuclear-localized protein capable of gene activation at transcriptional level," Gene, p. 21-29, (Feb. 10, 2000), vol. 245.
Jinrong Peng et al, "The Arabidopsis GAI gene defines a signaling pathway that negatively regulates gibberellin responses," Genes & Development, p. 3194-3205, (Feb. 10, 1997), vol. 11.

* cited by examiner

Primary Examiner—David T. Fox
(74) Attorney, Agent, or Firm—M. Todd Rands

(57) ABSTRACT

Methods for the production of reversibly male-sterile plants by introduction of a polynucleotide encoding a GA-insensitive mutant protein are disclosed along with nucleic acid constructs and transformed cells useful in the production of such plants. Also disclosed are the use of plants containing recombinant nucleic acid sequences in preventing pollination of plants with pollen containing one or more transgenes and in the introduction of economically important traits into elite varieties of plants.

14 Claims, 1 Drawing Sheet

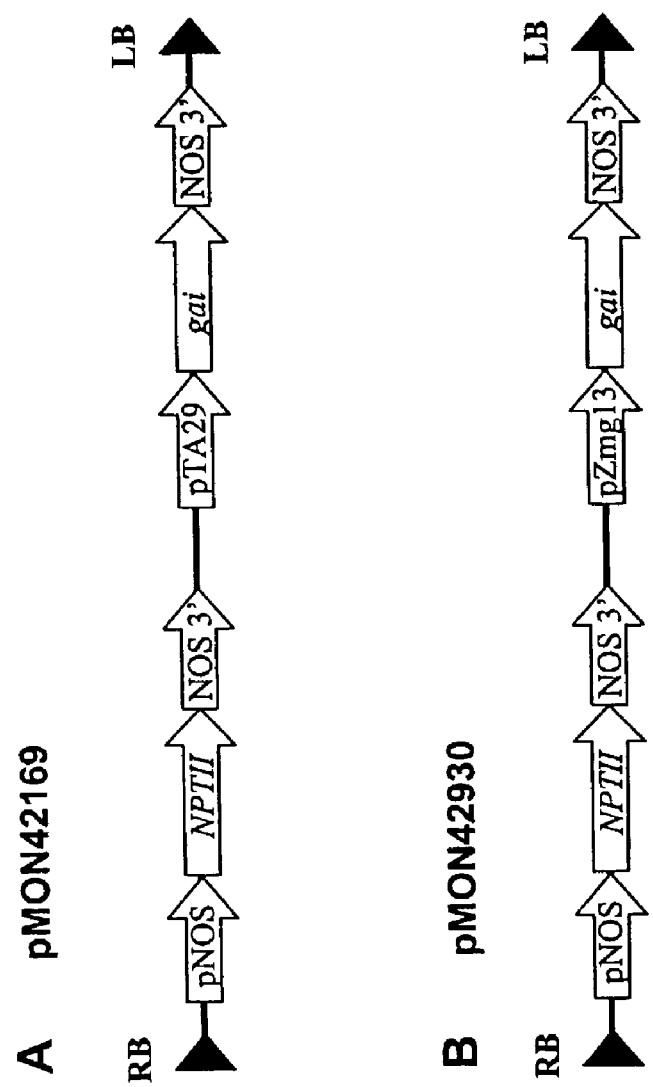

REVERSIBLE MALE STERILITY IN TRANSGENIC PLANTS BY EXPRESSION OF A GA-INSENSITIVE MUTANT PROTEIN, GAI.

This application claims priority to U.S. Provisional Application 60/331,953, filed Nov. 21, 2001, herein incorporated by reference in its entirety.

BACKGROUND OF INVENTION

Reversible male sterility is a valuable trait in the production of hybrid seed. Because phytohormones are believed to be involved in the plant male organ development, male sterility can potentially be induced by alteration of endogenous hormone levels or by alteration of responses to hormones. Several attempts have been made to chemically induce male sterility with the application of phytohormones (Moore, *Science*, 129:1738–1740, 1959; Eeninck et al., *Acta Bot. Neerla*, 27:199–204, 1978; Sawhney, *Can. J. Botany*, 61:1258–1265, 1981; Saini et al., *Aust. J. Plant Physiol.*, 9:529–537, 1974; Chandra Sekhar et al., *Sex. Plant Reprod.*, 4:279–283, 1991). Although these exogenous hormone treatments successfully produced male sterile plants, the narrow window of application, the necessity of applying chemicals continuously to produce sterility, lower seed yields on the treated plants after crossing, and occasional lapses in achieving complete sterility make hormonal induction of male sterility impractical for commercial hybrid seed production. The pleiotropic effects of the hormone applications as well as environmental influences on exogenous hormone uptake, translocation and metabolism likely cause these inconsistencies. The discovery of genes involved in hormone pathways and promoters conferring tissue-specific expression permit control of endogenous phytohormone levels in specific tissues, and allow precise, effective induction of male sterility. More importantly, male sterility induced by phytohormone perturbations can theoretically be reversed by application of the appropriate phytohormonal agonists or antagonists. Fertility restoration is critical as it enables inbred male sterile lines to be maintained.

The use of molecular biology to produce male sterility in plants has been described. In a series of patents, Cigan et al. disclose the use of the anther-specific promoter 5126 and variants thereof to control expression of sequences related to pollen formation (U.S. Pat. Nos. 5,689,049; 5,689,051; 5,763,243; 5,792,853; 5,795,753; 5,837,851; and 6,072,102). Albertson et al. (U.S. Pat. No. 5,962,769) describe a method for producing reversible male-sterile plants by introduction of an expression vector that produces avidin. Male sterility is reversed by crossing to a "restorer" line expressing anti-sense avidin or a suitable ribozyme. Alternatively, sterility can be reversed by application of biotin. Baudot et al. (U.S. Pat. No. 6,207,883) disclose the male fertility gene Ms41-A in *Arabidopsis* and a related maize gene Zm41-A. Baudot et al. further disclose that mutation of the Ms41-A gene resulted in male sterility. Michiels et al. (U.S. Pat. No. 6,025,546) utilized a method of transforming plants with a coregulating gene combined with a male sterility gene to generate a higher frequency of male sterile transgenic plants. Poovaiah et al. (U.S. Pat. No. 6,077,991) disclose the suppression of calcium/calmodulin-dependant protein kinase expression by the use of antisense constructs to induce male-sterility. Scott et al. (U.S. Pat. No. 5,955,653) disclose the use of a tapetum-specific callase gene and its promoter to induce male-sterility. Van Tunen et al. (U.S. Pat. No. 6,005,167) disclose a method for inducing male sterility by the use of recombinant polynucleotides that inhibit the expression of one or more genes involved in the synthesis of chalcone or one of its precursors.

It has been reported that sterility in many male sterile mutants is related to the decline of endogenous gibberellin (GA) levels (Nakajima et al., *Plant Cell Physiol.*, 32:511–513, 1991; Sawhney, *Can. J. Botany*, 70:701–707, 1992; Sawhney and Shukla, *Am. J. Botany*, 81:1640–1647, 1994) and that mutant plants could also lead to male sterility (Koornneef et al., *Physiol. Plant*, 65:33–39, 1985).

The gai gene isolated from *Arabidopsis* can negatively regulate GA responses (Peng et al., *Gene Dev.*, 11:3194–3205, 1997: WO 97/29123). The gai mutation of *Arabidopsis* confers a dwarf phenotype and a dramatic reduction in GA responsiveness (WO 97/29123). The gai is a gain-of-function mutation, and the wild-type allele (GAI) is dispensable. GAI encodes a polypeptide (GAI) of 532 amino acid residues. A 17-amino acid domain is missing in the gai mutant polypeptide. GAI contains several motifs characteristic of transcriptional coactivators, suggesting that GAI acts as a transcriptional regulator. The mutant gai appears to be resistant to GA regulation.

SUMMARY OF INVENTION

The present invention is based on the discovery that expression of gai in the male reproductive tissues of plants causes male sterility, and that fertility can be restored by kinetin, a synthetic cytokinin. The present invention is particularly useful as a rescuable male sterility system for hybrid seed production.

Among the several aspects of the invention is a method for producing a plant characterized by reversible male-sterility, comprising transforming a plant cell with a construct containing a polynucleotide encoding a gai gene and regenerating a plant from said plant cell wherein expression of said gai gene inhibits pollen formation in said plant and restoration of male-fertility is possible by application of cytokinins, for example kinetin.

The construct comprises a regulatory sequence and a termination sequence, both operably linked to polynucleotide encoding the gai gene. The regulatory sequence comprises a promoter. Suitable promoters can be selected from promoters that are constitutive, inducible, environmentally-regulated, developmentally-regulated, organelle-specific, cell-specific, tissue-specific, male specific, anther-specific, pollen-specific, stamen-specific, tapetum-specific or any combination thereof, for example, an inducible, male-specific promoter.

In a further aspect, the method further comprises transforming the plant cell comprising the construct encoding a gai gene with an additional nucleic acid construct comprising an inducible promoter and a transcription termination sequence both operably linked to an antisense construct, expression of which suppresses expression of the gai gene. Alternatively, a male-sterile plant is produced by sexually crossing a plant comprising a nucleic acid construct containing a polynucleotide encoding a gai gene with a plant, preferably of the same variety, comprising a nucleic acid construct containing an inducible promoter and a transcription termination sequence both operably linked to an antisense construct expression of which suppresses expression of the gai gene. In either case, male-fertility can be restored by expression of the antisense construct.

In another embodiment, the method further comprises transforming the plant cell comprising the construct encoding a gai gene with an additional nucleic acid construct comprising an inducible promoter and a transcription termination sequence both operably linked to a polynucleotide encoding a dominant negative mutant protein expression of which decreases expression or activity of the gai gene. Dominant negative mutations occur when a mutation expresses its effect even when it is heterozygous and expression of the mutation generally results in a decrease in the normal function. Alternatively, a male-sterile plant is produced by sexually crossing a plant comprising a nucleic acid construct containing a polynucleotide encoding a gai gene with a plant, preferably of the same variety, comprising a nucleic acid construct containing an inducible promoter and a transcription termination sequence both operably linked to a polynucleotide encoding a dominant negative mutant protein, expression of which decreases expression or activity of the gai gene. In either case, male-fertility can be restored by expression of the dominant negative mutant protein.

In yet another aspect, the method further comprises selfing the plant produced so as to produce offspring that are homozygous for the nucleic acid construct comprising a polynucleotide encoding the gai gene.

Another aspect provides a method for preventing or reducing the pollination of plants with pollen containing a transgene comprising interplanting, (1) a transgenic, male-sterile plant containing, in addition to at least one transgene, a recombinant construct encoding the gai gene, wherein said male-sterility is due to expression of said gai gene, and (2) a plant of the same or different variety as the plant in 1) which is not transgenic; and b) allowing the plants of 2) to pollinate the plants of 1).

Yet another aspect provides a method for preventing or reducing the pollination of plants with pollen containing a transgene, comprising obtaining a plant hemizygous for a pollen expressed gai gene linked to at least one transgene wherein expression of said gai gene results in abortion of transgenic pollen, which accounts for 50% of total pollen; and growing said plant.

A further aspect provides a method for producing a grain or plants with an economically important trait comprising interplanting (a) an agronomically desirable plant wherein said plant has been made reversibly male-sterile by any of the methods of the present invention, and (b) a plant possessing an economically desirable trait; and allowing the plants of (b) to pollinate the plants of (a).

Additional aspects include seeds from plants produced by any of the preceding methods, uniform populations of plants produced by any of the preceding methods, and hybrid plants produced by crossing plants produced by any of the preceding method with plants of a different variety.

BRIEF DESCRIPTION OF DRAWINGS

These and other features, aspects, and advantages of the present invention will become better understood with regard to the following description, appended claims and accompanying figures where:

FIG. 1A shows T-DNA regions of pMON42169.
FIG. 1B shows T-DNA regions of pMON42930.

DETAILED DESCRIPTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application are herein incorporated by reference in their entirety as if each individual publication, patent, patent application, database or other reference were specifically and individually indicated to be incorporated by reference.

The present inventors have discovered a method for producing plants with reversible male sterility by using techniques of plant molecular biology to introduce nucleic acid constructs encoding the gai gene and in particular the gai gene from *Arabidopsis*. Male sterility in these transformed plants is due to expression and accumulation of the gai gene product, which leads to a decrease in response to gibberellin (GA) in the plant. Because GA is needed for normal anther development and pollen formation, a decrease in response to GA is thought to result in a failure of anther development and normal pollen formation. Male fertility is found to be restored by the application of natural or synthetic cytokinins, for example kinetin, not by GAs.

The technology disclosed creates a new method for generating and maintaining male sterility in plants. The method can not only reduce the expense of seed production for existing hybrid plants such as corn, but also makes it possible to produce hybrid varieties of traditionally non-hybrid crops.

There are many ways that gai generated reversible male sterility can be used in the production of hybrid seed. One example is the use of gai linked to an anther-specific promoter. When expressed in the anthers, gai acts as a dominant male-sterility gene. Homozygous male-sterile female lines can be maintained, for example, by the use of chemical fertility restoration as described herein. The homozygous male-sterile female line is crossed with isogenic wild type plants to produce a hemizygous male-sterile female line. In hybrid seed production fields, the hemizygous line is crossed with a male line to produce F1 hybrid seeds. When planted, 50% of the resulting plants will be male-sterile; however, in species such as corn that produce an excess of pollen, the remaining 50% of the plants that are male fertile will provide sufficient pollen for pollination and thus normal yields. Furthermore, it has been suggested that out-crossed male sterile corn plants have a yield advantage over fertile plants due to resource reallocation from abolishing the development of male tissues (Hunter et al., *Agron. J.*, 65:471–472, 1973). Thus a hybrid population composed of 50% male steriles has the potential to deliver increased yields.

Another example is the use of gai driven by a pollen-specific promoter, in which case only homozygous plants are male sterile. Homozygous male-sterile female lines are produced by selfing hemizygous lines and then the lines are maintained through restoration of male fertility, for example, by chemical restoration as described herein. The homozygous male-sterile female line is then crossed with a male line to produce F1 hybrid seed. This seed will result in fertile F1 hybrids with 50% sterile pollen.

A variety of different methods can be employed to introduce polynucleotides into plant protoplasts, cells, callus tissue, leaf discs, meristems, etc., to generate transgenic plants. These methods include, for example, *Agrobacterium*-mediated transformation, particle gun delivery, microinjection, electroporation, polyethylene glycol-mediated protoplast transformation, liposome-mediated transformation, etc. (Potrykus *Annu. Rev. Plant Physiol. Plant Mol. Biol.*

42:205, 1991; Maliga et al., *Methods in Plant Molecular Biology*, Cold Spring Laboratory Press, 1995).

In general, transgenic plants comprising cells containing isolated polynucleotides, vectors or expression cassettes of the present invention can be produced by transforming plant cells with a DNA construct as described herein via any of the foregoing methods; selecting plant cells that have been transformed on a selective medium; regenerating plant cells that have been transformed to produce differentiated plants; and selecting transformed plants that are male-sterile. Specific methods for transforming a wide variety of dicots and obtaining transgenic plants are well documented in the literature (Gasser and Fraley, *Science* 244:1293, 1989; Fisk and Dandekar, *Scientia Horticulturae* 55:5, 1993; Christou, *Agro Food Industry Hi Tech*, p. 17, 1994; and the references cited therein).

Successful transformation and plant regeneration have also been achieved in some monocots including maize (*Zea mays*; Gordon-Kamm et al. (1990) *Plant Cell* 2: 603; Fromm et al. (1990) *Bio/Technology* 8:833).

Nucleic acid constructs of the present invention can be part of vectors and in particular expression vectors or expression cassettes. In plants, transformation vectors capable of introducing polynucleotides encoding a gai gene are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally, a 5' non-translated leader sequence; a nucleotide sequence that encodes a protein of interest; and a 3' non-translated region that encodes a polyadenylation signal that functions in plant cells to cause the termination of transcription and the addition of polyadenylate nucleotides to the 3' end of the mRNA encoding the protein. Plant transformation vectors also generally contain a selectable marker. Typical 5' to 3' regulatory sequences include a transcription initiation start site, a ribosome binding site, an RNA processing signal, a transcription termination site, and/or a polyadenylation signal. Vectors for plant transformation have been reviewed in Rodriguez et al. (1988) *Vectors: A Survey of Molecular Cloning Vectors and Their Uses*, Butterworths, Boston; Glick et al. (1993) *Methods in Plant Molecular Biology and Biotechnology* CRC Press, Boca Raton, Fla.; and Croy (1993) In *Plant Molecular Biology Labfax*, Hames and Rickwood, Eds., BIOS Scientific Publishers Limited, Oxford, UK. Non-limiting examples of plant transformation vectors useful in the present invention include pMON42169 and pMON42930, shown in FIG. 1A and FIG. 1B, respectively.

Promoters useful in the present invention include those that confer appropriate cellular and temporal specificity of expression. Such promoters include those that are constitutive, inducible, environmentally regulated, developmentally regulated, organelle-specific, cell-specific, tissue-specific, male-specific, anther-specific, pollen-specific, stamen-specific, tapetum-specific or any combination of the preceding, for example an inducible, male-specific promoter. Such promoters are well known to those of ordinary skill in the art. An example of a male-specific regulatory region can be found in U.S. Pat. No. 6,037,523. Examples of anther-specific promoters and regulatory sequences are disclosed in U.S. Pat. Nos. 6,072,102; 5,962,769; 5,837,851; 5,795,753; 5,639,948; 5,589,610; 5,477,002; 6,013,859; 5,659,124; and 5,824,542. Examples of pollen-specific promoters are disclosed in U.S. Pat. Nos. 5,412,085; 5,086,169; 5,545,546; 6,018,104; 5,977,433; 5,545,546; and 5,086,169. Additional disclosure of pollen-specific promoters can be found in McCormick (*Trends Genet.*, 2:298–303, 1991), Hamilton et al. (*Sex. Plant Reprod.*, 2:208, 1989), Guerrero et al. (*Molec. Gen. Genet.*, 224:161–168, 1990), Weterings et al. (*Plant Molec. Biol.*, 18:1101–1111, 1992), and Shen et al. (*Molec., Gen. Genet.*, 234:379–389, 1992). Examples of tapetum-specific promoters and regulatory sequences can be found in U.S. Pat. Nos. 5,470,359; 5,639,948; 5,589,610; and European Patent No. 0,344,029. Further examples of tapetum-specific promoters and regulatory sequences can be found in Koltunow et al. (*Plant Cell*, 2:1201–1224, 1990), Hird et al. (*Plant J.*, 4:1023–1033, 1993), Paul et al. (*Plant Molec. Biol.*, 19:611–622, 1992), and Seurinck et al. (*Nucl. Acids Res.*, 18:3403, 1990). Examples of stamen-specific promoters can be found in U.S. Pat. Nos. 5,639,948; 5,589,610; 5,880,331; 6,025,546; European Patent No. 0,344,029; and PCT Publication Nos. WO92/13956 and WO92/13957. In one embodiment, the pollen-specific promoter pZmg13 (Hanson et al., *Plant Cell*, 1:173–170, 1989) is used. In another embodiment, the anther-specific promoter pTA29 (Koltunow et al., *Plant Cell*, 2:1201–1224, 1990) is used.

Any nucleic acid sequence encoding a GA-insensitive protein active in the plant of interest can be used. The sequence used can be the coding region for the protein or can be a mutated and/or truncated form of the protein as long as the mutated and/or truncated form retains GA-insensitive activity. Polynucleotide sequences encoding gai genes are known in the art and can be found, for example, in the GenBank data base maintained by the National Biotechnology Information Center available to the public at http://www.ncbi.nlm.nih.gov/ and the data bases maintained at the European Bioinformatics Institute and available to the public at http://www.ebi.ac.uk/. In addition, sequence data for gai has been published by Harberd et al. (WO 97/29123).

Although male sterility is the preferred method for the production of hybrid seed due to its low labor cost and high seed production, the difficulty in maintaining male sterile inbred parental lines, however, has in the past limited its use for commercial applications. Using the methods of the present invention, maintenance of homozygous male sterile female lines is greatly simplified. Fertility can be restored in male-sterile lines by the application of cytokinins. Cytokinins used to restore fertility can be either naturally occurring or synthetic. Synthetic cytokinins include those made by recombinant DNA technology as well as those made by conventional chemical synthesis. Cytokinins can be conveniently applied to large numbers of plants in the form of a spray. In addition to the cytokinin and a suitable diluent, the spray can also contain other ingredients such as a surfactant to increase uptake of the cytokinin. Cytokinin can be used in a single application or in multiple applications. Cytokinin can be applied prior to development of the male organs of a plant. In one embodiment, the synthetic cytokinin kinetin is applied at a rate ranging between about 1 mg/plant to about 50 mg/plant, preferably about 10 mg/plant to about 15 mg/plant to restore male fertility.

Male fertility can also be restored by the use of a second recombinant construct (restorer construct) that inhibits or interferes with expression of the construct encoding the gai gene. In one embodiment, the restorer construct is operably linked to an inducible promoter so that application of the proper stimulus to drive expression of the restorer construct can be used restore male fertility.

In one embodiment, the restorer construct encodes an antisense sequence. Antisense sequences can be produced by reversing the orientation of the transcribed region of a gene or polynucleotide sequence whose suppression is desired. When operatively coupled to a suitable inducible transcriptional promoter such as discussed herein, a transcript of the antisense DNA strand is produced when desired to restore fertility. The production and use of antisense DNA is well known in the art and can be found, for example, in Green et al. ((1986) *Annu. Rev. Biochem.* 55:569). The transcript of the antisense DNA is antisense RNA. Without being bound by theory, it is believed that an individual antisense RNA molecule may hybridize with a complementary "sense" mRNA molecule to form an RNA—RNA duplex. Such a duplex may prevent the sense mRNA molecule from, for example, being translated or binding to another nucleic acid such as DNA. The presence of RNA—RNA duplexes may also initiate a sequence-specific RNA degradation pathway with the antisense molecules or the RNA—RNA duplexes playing a role in initiating the degradation pathway, and both sense and antisense molecules serving as specific targets for degradation.

Waterhouse et al. (*Proc. Natl. Acad. Sci. USA,* 95:13959–13964, 1998) reported that the most efficient gene silencing was achieved in plants by simultaneous expression of sense and antisense RNA. Without being bound by theory, this efficiency is thought to be due to the formation of double stranded (ds) RNA. Thus the presence in plants of the present invention of sense and antisense constructs encoding the gai gene is thought to result in a high efficiency of gai inhibition.

Although the previous discussion has for the most part described the formation of dsRNA between full length transcripts, it will be apparent to one of ordinary skill in the art that the antisense transcript need not encompass the entire sense sequence but may be a fragment that hybridizes to only a portion of the sense RNA. The antisense transcript should be of sufficient length to allow specificity in binding to the target (sense) transcript. In general, the antisense transcript should be at least 10 bases long, more preferably at least 20 bases long, although the presence of rare sequences may allow the use of shorter antisense transcripts. The use of this technology to suppress the expression of specific plant genes has been described, for example in European Patent Publication No 271988; U.S. Pat. Nos. 5,073,676, 5,107,065 and 5,569,831; PCT Publication WO 00/49035, Smith et al. ((1988) *Nature,* 334,724 Smith et al. ((1990) *Plant Mol. Biol.* 14,369. In another embodiment, male fertility may be achieved by the use of a restorer construct containing a dominant negative mutation. Expression of a restorer construct containing a dominant negative mutation generates a mutant transcript that, when coexpressed with the gai gene inhibits the action of the gai transcript. Methods for the design and use of dominant negative constructs are well known in the art and can be found, for example, in Herskowitz (*Nature,* 329:219–222, 1987) and Lagna and Hemmati-Brivanlou (*Curr. Topics Devel. Biol.,* 36:75–98, 1998).

In another embodiment, the restorer construct encodes a ribozyme that cleaves the recombinant gai transcript. Ribozymes are catalytic RNA molecules that can promote specific biochemical reactions without the need for auxiliary proteins. Reactions catalyzed by ribozymes can be either intramolecular or intermolecular. Examples of intramolecular reactions are self-splicing or self-cleaving reactions whereas intermolecular reactions involve other RNA molecules as substrates and more closely approximate true enzymatic reactions where the enzyme is unchanged after each reaction. In the present method, ribozymes catalyzing intermolecular reactions are preferred. The use of ribozymes to alter expression of genes is discussed in Cech (*J. Am. Med. Assoc.,* 260:3030–3034, 1988).

In addition to the method for producing reversible male sterility in transgenic plants, plants produced by the method disclosed herein are also considered within the scope of the present invention. Such plants can be produced by the methods described above and contain a recombinant construct encoding a gai gene. Optionally, the plant can further comprise a restorer construct such as those described above. Such plants can be either of the class dicotyledonae (dicots) or the class monocotyledonae (monocots). When first produced, the plant will be hemizygous for the introduced recombinant constructs. Such plants, however, can be made homozygous by "selfing," a technique that is well known in the art of plant breeding. Also within the scope of the present invention are uniform populations of plants that have been altered by the methods of the present invention such that they possess reversible male sterility.

Also included within the scope of the present invention are seeds and progeny from any of the above described plants. Another aspect of the present invention encompasses a method for the production of a hybrid plant comprising sexually crossing a plant having reversible male sterility and produced by the methods described herein with a plant of a different variety as well as the hybrid plants produced, uniform populations of such hybrid plants, and seeds from such hybrid plants.

The present invention also provides a method for preventing or reducing cross-pollination of transgenic plants with wild type plants. With the increasing introduction of transgenic plants into production agriculture, there has been concern about the possible effects due to cross pollination between transgenic and wild type plants. Using the present methods, transgenic male sterile plants can be produced and planted together with a small number of non-transgenic plants to act as pollen donors. In this way, only wild type pollen would be released into the environment. By way of a non-limiting example, a transgenic hybrid plant combining insect resistance and an anther-expressed gai gene can be produced using the methods described herein. Interplanting with a small number of non-transgenic hybrids would provide a "refuge" for resistant management as well as pollen donors for complete pollination in the production field of the transgenic plants. Because the transgenic plants would be male-sterile, there would be no or greatly reduced pollination of wild type plants with transgenic pollen. As used herein in reference to cross-pollination "reduced" means that the incidence of pollination of wild type plants by transgenic pollen is less than occurs in the absence of an anther- or pollen-expressed gai gene.

Similar results can be obtained using a plant that is hemizygous for a desirable transgene linked to a pollen-expressed gai. In this situation, only wild type pollen and not pollen producing the transgene linked to the expressed gai gene would be produced. In one preferred embodiment, the transgene and pollen expressed galare under the control of different regulatory sequences so that whereas the gai is expressed primarily or preferably only in pollen, the transgene is expressed in a wider variety of cell types. In this way, pollination of wild type plants with transgenic pollen can be avoided or reduced. Such plants can be produced by transforming plant cells with the linked transgene and pollen expressed gai by any of the methods described herein, and regenerating a plant from said transformed cells. Alternatively, such plants can be produced by sexually crossing a plant homozygous for the linked transgene and pollen expressed gai with a homozygous wild type (non-transgenic) plant to produce a hemizygous hybrid.

Linkage, as is well known in the art, refers to the situation in which two genes or segments of DNA are inherited together. Linked genes or DNA segments are located on the same chromosome and are generally located within 50 centiMorgans (cM) of each other. As used herein the term "linked" in reference to genes and DNA segments means that the genes and/or segments are located on the same chromosome within 50 cM, perferably 10 cM, more preferably 2 cM, and, more preferably still, 0.1 cM of each other.

As used herein, the term "transgenic" refers to a plant whose germline contains a gene or nucleic acid construct introduced using recombinant DNA technology. As used herein the term "transgene" means a gene or DNA construct that has been introduced into the germlne of a plant using recombinant DNA technology.

The present methods are also useful in the introduction of economically valuable traits from plants having, in general, undesirable production characteristics into plants having desirable characteristics (elite plants or varieties) and in particular elite hybrids. This method of introducing valuable traits is detailed in U.S. Pat. Nos. 5,704,160 and 5,706,603; both of which are herein incorporated by reference.

An example of the use of this method can be found in corn. Most varieties of corn grown commercially are developed to meet common manufacturing and feeding requirements. There exists, however, a market for specialty varieties that differ from standard varieties by the presence of one or more economically important transgenic or non-transgenic traits. In corn, such traits include, but are not limited to, degree of starch branching, increased accumulation of sugars or water-soluble polysaccharides, degree of endosperm hardness, protein or amino acid content, and oil content. Unfortunately, many plants that possess these economically important traits also possess characteristics that make them agronomically undesirable. The method provides a means to circumvent this problem by capturing economically important traits from agronomically inferior plants through elite varieties. An elite variety, as is well known in the art, is a variety that possess a favorable combination of traits making it particularly useful in commercial production.

In this method, male-sterile plants of an elite variety are interplanted with a low density of male-fertile plants having the desired trait. By "low density" is meant that the male-fertile plants are interplanted at a rate that does not exceed about 10 male-fertile plants per 100 male-sterile plants. Due to low density planting, the presence of the agronomically inferior plants does not significantly reduce overall yields. The reversible male-sterility of the present invention is particularly useful in production of high value plants and grains by this method. For example, a agronomically elite variety, preferably a hybrid variety, that has been made reversibly-male sterile by the methods of the present invention can be randomly interplanted with a agronomically inferior variety that possesses a desirable trait and that is present in the field at a low density. The inferior variety is allowed to pollinate the elite variety, allowing the economically important trait to be expressed in the plant and/or grain produced.

EXAMPLES

The following examples are intended to provide illustrations of the application of the present invention. The following examples are not intended to completely define or otherwise limit the scope of the invention.

Example 1

Vector Construction

An *Arabidopsis* gai mutant (Koornneef et al., *Physiol. Plant,* 65:33–39, 1985) obtained from *Arabidopsis* Biological Resource Center (The Ohio State Univ., Columbus, Ohio) was used to prepare floral RNA for the isolation of gai cDNA by RT-PCR. The RT-PCR was performed using primers designed based on published gai sequence (Peng et al., *Gene Dev.,* 11:3194–3205, 1997). The cDNA was confirmed by sequencing and subcloned into expression cassettes driven by either the pollen-specific pZmg13 promoter (Hanson et al., *Plant Cell,* 1:173–179, 1989) or the anther-specific pTA29 promoter (Koltunow et al., *Plant Cell,* 2:1201–1224, 1990), and terminated by the nopline synthase sequence (NOS3"). Approximately 1.5- and 1.0-kb upstream sequences of TA29 and Zmg13 coding regions were adapted in these expression cassettes, respectively. The resulting gai expression cassettes were cloned into binary vectors using an enhanced CaMV 35S promoter (e355)-driven NPTII as the selectable marker to generate pMON42169 (FIG. 1A) and pMON42930 (FIG. 1B). All other genetic elements used in the binary vector were identical to those described by Ye et al. (*Plant J.,* 19:249–257, 1999).

Example 2

Transformation, Plant Material and Growth Conditions

The binary vectors pMON42169 and pMON42930 were electroporated into *Agrobacterium tumefaciens* ABI strain. The *Agrobacterium* strain harboring pMON42169 was transformed into leaf discs of *Nicotiana tabacum* cultivar "samsun" by the co-cultivation method (Horsch et al., *Science,* 227:1229–1231, 1985). R0 male sterile transgenic plants were pollinated by wild-type pollen to produce F1 seeds. All of the plants were grown in greenhouses at 28/21° C. (day/night) with a 16-hr photoperiod (400 µmol $m^{-2}sec^{-1}$) and 50% relative humidity. To identify the transgenic plants in the following generations, seeds were surface sterilized and germinated on Murashige and Skoog medium (M0404, Sigma, St. Louis, Mo.) containing 100 mg/L of kanamycin.

*Arabidopsis thaliana* plants, ecotype Columbia, were grown in a growth chamber at 24° C. with a 16-hr photoperiod (120 µmol $m^{-2}sec^{-1}$) and 70% relative humidity. The binary Ti plasmids pMON42169 and pMON42930 were introduced into *Arabidopsis* via *Agrobacterium*-mediated vacuum infiltration (Bechtold et al., *C R Acad Paris Life Sci.,* 316:1194–1199, 1993). To select the transgenic plants, seeds collected from vacuum infiltrated plants were surface sterilized and germinated on Murashige and Skoog medium (M0404) containing 50 mg/L of kanamycin.

Among 22 independent kanamycin resistant R0 transgenic plants generated in tobacco with pMON42169, 18 plants displayed a male sterile phenotype. Three of the male sterile plants were also slightly shorter. F1 plants resulting from crosses with wild-type pollen inherited the male-sterile phenotype. These male-sterile transgenic plants did not produce any visible pollen. Except for line 775, which is derived from one of the slightly dwarf R0 plants, the height of the transgenic plants is comparable to wild-type.

Most of the transgenic plants remained morphologically similar to wild-type plants except for the male-sterile phenotype. The production of F1 seeds of the transgenic plants by fertilization with wild-type pollen suggested that the female reproduction was not affected. The floral, anther and pistil development of lines 788 and 790 were monitored along with wild-type plants. By measuring weight and length at various stages, floral and pistil development of these transgenic plants were similar to wild-type plants. On the other hand, the anthers of these transgenic plants were noticeably smaller and lighter as early as stage 1. This was consistent with the TA29 promoter expression profile mentioned earlier. It appeared that altering GA responses by expressing gai in the anthers did not result in any other pleotropic effects normally associated with hormonal changes.

To test if the gai-induced male sterility could be applied to other species, the same binary vector, pMON42169, used in tobacco transformation was also introduced into *Arabidopsis*. Complete male sterility was observed in 7 of the 17 transgenic *Arabidopsis* plants generated. Most of these male sterile plants also showed other phenotypes similar to GA-deficient mutants. For example, the transgenic male sterile flowers had shorter filaments. These phenotypes could be the result of leaky expression of the TA29 promoter in *Arabidopsis*. However, the female reproductive tissues of these plants remained normal and were able to set seed by applying wild-type pollen. Restoration of fertility may be achieved by kinetin applications. A maize pollen-specific promoter may also be used to express gai (FIG. 1B). Twenty-five of 32 transgenic plants containing the construct exhibited a partial pollen abortion phenotype. Seventeen plants had approximately 50% pollen abortion, which was probably caused by the gametophytic expression of a single insertion of the transgene. Although detailed molecular and genetic characterizations have not been completed, this is probably the most direct evidence of GA"s involvement in pollen development.

Example 3

Plant RNA and DNA Isolation and Analysis

Genomic DNA was isolated from leaves of tobacco plants using the DNeasy Plant Mini Kit (Qiagen, Valencia, Calif.). Genomic DNA (30 μg) was digested with BamHI, separated on a 0.8% (W/V) agarose gel, and transferred to positively charged nylon membranes (Roche Molecular Biochemicals, Indianapolis, Ind.). The probe used in the hybridization was prepared by PCR corresponding to the NPTII coding region. Prehybridization, hybridization, washing and detection of the membrane were conducted by using the non-radioactive DIG system from Roche Molecular Biochemicals following manufacturer's protocols.

Total RNA was isolated from anthers at stages between –1 and +2 by TRIzol Reagent from Life Technologies (Gaithersburg, Md.) following manufacturer's protocols. Total RNA samples (10 □g) were electrophoresed on a 1.2% (W/V) agarose/formaldehyde gel and transferred to a positively charged nylon membrane (Roche Molecular Biochemicals). The probe used in the hybridization was prepared by PCR corresponding to gai coding region. The blot was analyzed by the same DIG system as used in the DNA gel blot analysis.

Because the TA29 promoter initiates transcription at stage –2 of tobacco anther development, total RNA was isolated from anthers between stage –1 and +2 for RNA gel-blot analysis. All five of the transgenic plants (pMON42169) showed strong expression of gai. The absence of a detectable band on the gel blot of the wild-type plant indicated that the gai message was from the expression of the gai transgene. A DNA gel blot analysis was also performed on some of the transgenic plants. Lines 775 and 786 had multiple copies of transgenic integration whereas lines 788 and 790 both contained a single copy of the transgene.

Example 4

Fertility Restoration

Kanamycin resistant F1 seedlings were transferred to soil and grown to flowering stage. After male sterility in the first few flowers was observed, plants from each lines were divided into four groups to receive different treatments every other day. One group received 15 mg of kinetin (a synthetic cytokinin) (Sigma) per plant, while the other two groups received either 10 mg of $GA_3$ (Sigma) or 10 mg of TDZ (Sigma) per plant. The chemicals are in an aqueous solution containing 0.25% of Sylgard 309 surfactant (Willbur-Ellis, Fresno, Calif.) and the last group received surfactant only. The applications continued for two weeks.

As expected, exogenous $GA_3$ application did not restore the anther development of transgenic plants. The $GA_3$-treated transgenic plants were spindly but remained male sterile. This confirmed that the male sterility exhibited by the transgenic plants was not due to the reduction of endogenous GA levels. However, when sprayed with kinetin, a synthetic cytokinin, the male sterile transgenic plants shed pollen and set seeds. On the other hand, TDZ, which is thought to increase plants" cytokinin levels by inhibiting the degradation of cytokinins, did not restore the fertility of the male sterile plants.

In another experiment, F1 plants from several male sterile transgenic lines were selected based on resistance to kanamycin and grown to flowering to verify the inheritance of the male sterile phenotype. Each plant was then sprayed with a solution containing 15 mg of kinetin every other day for two weeks. The plants continued to develop male sterile flowers until 10 days after the first application of kinetin. At 10 days post-application, the flowers that developed were male fertile. Flowers from treated plants began visibly shedding pollen whereas untreated flowers remained sterile. Under greenhouse growth conditions, the transition from stage –3 to stage 12 for a tobacco floral bud occurred in approximately 10 days. It appeared that for effective fertility restoration, kinetin needed to be applied prior to stage –2, which coincided with the onset of the TA29 promoter. Furthermore, the production of male fertile flowers persisted for 11 days post-application, indicating that continuous kinetin treatments were not necessary for restoring the fertility of these male sterile plants.

The kinetin-restored flowers not only were morphologically normal but also had typical seed sets. When the selfed seed of kinetin-restored flowers were compared with the crossed seed of sterile flowers and the selfed seed of wild-type flowers, no significant difference was observed in seed weight (Table 1). To simplify the segregation analysis, lines 788 and 790, which were shown to have a single copy of the transgene, were included in the experiments. Both lines had seedling ratios of kanamycin resistant vs. susceptible at 1:1 from crossing and 3:1 from selfing. These ratios correlate with the expected Mendelian ratios for segregation of a single dominant gene. These analyses further demonstrate the specificity of the TA29 promoter during a particular period of anther development.

TABLE 1

Seed yields of male sterile transgenic plants resulted from crosses (C) with wild-type pollen and selfing (S) after fertility restoration by kinetin application

| Event | Seed weight (mg)[a] | (Kan$^r$/Kan$^s$)[b] | $x^2$ |
|---|---|---|---|
| 788 (C) | 122.6 ± 10.9 | 84/81 | 0.05 (1:1) |
| 782 (S) | 113.0 ± 18.9 | 115/41 | 0.14 (3:1) |
| 790 (C) | 132.2 ± 17.2 | 82/86 | 0.10 (1:1) |
| 790 (S) | 110.2 ± 13.5 | 133/38 | 0.81 (3:1) |
| wild-type (S) | 124.4 ± 15.7 | — | — |

[a]Numbers represent the mean of 5 seed sets ± SE.
[b]Media grown seedlings were assayed for the presence or absence of the selectable marker kanamycin
Kan$^r$, kanamycin resistant
Kan$^s$, kanamycin sensitive In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. Whereas some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

The invention claimed is:

1. A method for producing a plant characterized by reversible male-sterility, said method comprising:
    transforming a plant cell with a nucleic acid construct containing a polynucleotide comprising a gai gene from *Arabidopsis*, operably linked to an anther-specific regulatory sequence and transcription termination sequence; and
    regenerating a plant from said plant cell wherein expression of said gai gene inhibits pollen formation in said plant.

2. A method for producing a plant characterized by reversible male-sterility, said method comprising:
    transforming a plant cell with a nucleic acid construct containing a polynucleotide comprising a gai gene from *Arabidopsis*, operably linked to an anther-specific regulatory sequence and transcription termination sequence;
    regenerating a plant from said plant cell wherein expression of said gai gene inhibits pollen formation in said plant; and
    restoring male-fertility by application of a composition comprising kinetin.

3. The method of claim 2, wherein said composition further comprises a surfactant.

4. The method of claim 2, wherein kinetin is applied at between about 1 mg/plant to about 50 mg/plant.

5. The method of claim 2, wherein kinetin is applied at between about 10 mg/plant to about 15 mg/plant.

6. The method of claim 2, wherein said composition is applied prior to development of the male tissues.

7. The method of claim 2, wherein said composition is applied during the development of male tissues.

8. A method for producing a plant characterized by reversible male-sterility, said method comprising:
    transforming a plant cell with a nucleic acid construct containing a polynucleotide comprising a gai gene from *Arabidopsis*, operably linked to an anther-specific regulatory sequence and transcription termination sequence;
    regenerating a plant from said plant cell wherein expression of said gai gene inhibits pollen formation in said plant;
    restoring male-fertility by application of a composition comprising kinetin; and
    selfing said plant to produce a plant homozygous for said polynucleotide comprising a gai gene.

9. A seed from a plant produced by the method of any one of the preceding claims, wherein said seed comprises said nucleic acid construct.

10. A uniform population of plants produced by the method of any one claims 1, 2, 3, 4–7 or 8.

11. A method of producing a hybrid plant said method comprising:
    sexually crossing a plant produced by the method of any one of claims 1, 2, 3, 4–7, or 8 with a plant of the same species having a different genetic makeup.

12. A hybrid plant produced by the method of claim 11.

13. A seed produced from the plant of claim 11, wherein said seed comprises said nucleic acid construct.

14. A transgenic corn plant expressing the *Arabidopsis* gai gene specifically in the anther tissue of said plant, wherein the female reproductive tissues of said corn plant are functional, but the male reproductive tissues are not functional, relative to the corresponding tissues in a corn plant that does not express the gai gene in the anther tissue.

* * * * *